(12) United States Patent
Cen et al.

(10) Patent No.: US 9,050,328 B2
(45) Date of Patent: Jun. 9, 2015

(54) PHARMACEUTICAL COMPOSITION FOR IMPROVING DISSOLUTION RATE OF PRASUGREL AND ITS PREPARATION METHOD

(75) Inventors: Junda Cen, Jiangsu (CN); Chun-hong Zhang, Jiangsu (CN); Qi Zhang, Jiangsu (CN); Aifeng Lü, Jiangsu (CN)

(73) Assignee: Jiangsu Hansoh Pharmaceutical Group Co., Ltd., Jiangsu (CN)

( * ) Notice: Subject to any disclaimer, the term of this patent is extended or adjusted under 35 U.S.C. 154(b) by 0 days.

(21) Appl. No.: 13/643,197

(22) PCT Filed: Apr. 22, 2011

(86) PCT No.: PCT/CN2011/073162
§ 371 (c)(1),
(2), (4) Date: Oct. 24, 2012

(87) PCT Pub. No.: WO2011/134369
PCT Pub. Date: Nov. 3, 2011

(65) Prior Publication Data
US 2013/0045251 A1    Feb. 21, 2013

(30) Foreign Application Priority Data

Apr. 27, 2010  (CN) .......................... 2010 1 0158669

(51) Int. Cl.
| | | |
|---|---|---|
| A61K 31/4365 | (2006.01) | |
| A61K 47/48 | (2006.01) | |
| A61K 9/14 | (2006.01) | |
| A61K 9/20 | (2006.01) | |
| B82Y 5/00 | (2011.01) | |
| A61K 9/16 | (2006.01) | |

(52) U.S. Cl.
CPC ............ *A61K 31/4365* (2013.01); *A61K 9/145* (2013.01); *A61K 9/2018* (2013.01); *A61K 47/48969* (2013.01); *A61K 9/2054* (2013.01); *A61K 9/146* (2013.01); *A61K 9/1694* (2013.01); *B82Y 5/00* (2013.01)

(58) Field of Classification Search
None
See application file for complete search history.

(56) References Cited

U.S. PATENT DOCUMENTS

| 5,070,081 A | * | 12/1991 | Majid et al. .................. 514/58 |
| 2010/0062066 A1 | * | 3/2010 | Bernstein et al. ............ 424/486 |
| 2011/0124675 A1 | * | 5/2011 | Zhao .......................... 514/301 |

FOREIGN PATENT DOCUMENTS

| CN | 101456864 A | 6/2009 | |
|---|---|---|---|
| CN | 101554378 A | 10/2009 | |
| CN | 101633662 A | 1/2010 | |
| CN | 101810611 A | 8/2010 | |
| WO | WO 2008/060934 A2 | 5/2008 | |
| WO | WO 2010015144 A1 * | 2/2010 | ........... C07D 495/04 |

OTHER PUBLICATIONS

Folttmann et al., "Polyvinylpyrrolidone (PVP)—One of the Most Widely Used Excipients in Pharmaceuticals: An Overview", Jun. 2008, Drug Delivery Technology, vol. 8, No. 6, pp. 22-27.*
International Search Report for International Application No. PCT/CN2011/073162, dated Aug. 4, 2011 (4 pages).
Formulation containing a thienopyridine antiplatelet prodrug. IP.com Journal (2010), 10(8A), 32 (No. IPCOM000198165D), Jul. 28, 2010.

* cited by examiner

*Primary Examiner* — Michael B Pallay
(74) *Attorney, Agent, or Firm* — Brinks Gilson & Lione

(57) ABSTRACT

A pharmaceutical composition containing prasugrel and its pharmaceutically acceptable salts, and methods for preparing the same are disclosed. The pharmaceutical composition improves the dissolution rate of prasugrel and its salts at high pH by using solid dispersion technology, inclusion technology or adding surfactants.

22 Claims, No Drawings

PHARMACEUTICAL COMPOSITION FOR IMPROVING DISSOLUTION RATE OF PRASUGREL AND ITS PREPARATION METHOD

REFERENCE TO EARLIER FILED APPLICATIONS

This application is a 371 national phase of PCT/CN2011/073162, filed Apr. 22, 2011, and claims the benefit of Chinese Application No. 201010158669.5, filed Apr. 27, 2010, the disclosures of which are incorporated, in their entirety, by this reference.

FIELD OF THE INVENTION

This invention relates to a pharmaceutical composition containing prasugrel and its salts, and preparation methods for the same. Specially, this invention relates to a pharmaceutical composition with improved dissolution characteristics of prasugrel and its salts at high PH using solid dispersion technology, inclusion technology, and surfactant technology, and methods of preparing the pharmaceutical compositions.

BACKGROUND OF THE INVENTION

The chemical name of prasugrel is 5-(2-cyclopropyl-1-(2-fluorophenyl)-2-oxoethyl)-4,5,6,7-tetrahydrothieno[3,2-c]pyridin-2-yl acetate and is shown below.

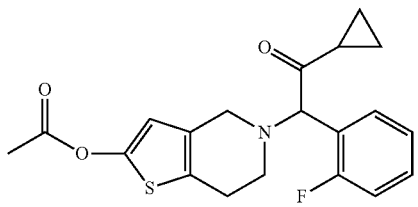 [SMILES: CC(=O)Oc1cc2c(s1)CCN(C(C(=O)C1CC1)c1ccccc1F)C2]

Its molecular formula is $C_{20}H_{20}FNO_3S$, and its molecular weight is 373.44.

Prasugrel is an oral platelet inhibitor and an anticlotting drug. It was originally developed for patients suffering from acute coronary syndrome who need percutaneous coronary intervention, including patients who need stent placement. Research results show that prasugrel could reduce the death resulting from nonfatal heart disease and stroke more effectively than clopidogrel, and decrease the stent thrombosis risk.

Eli Lilly filed a patent application US 2008176893 relating to prasugrel hydrochloride in 2006, in which it claimed a formulation and method of administration. A film-coated, diamond-shaped tablet of 5 or 10 mg prasugrel hydrochloride (prasugrel, Efient) is currently available in Europe and the USA. A single loading dosage of 60 mg is typically followed by maintenance doses of 10 mg per day. At the same time, 75-325 mg aspirin is co-administrated every day. Prasugrel hydrochloride is slightly soluble at pH 1-4, very slightly soluble in pH 5 and insoluble in pH 6-7. The hydrochloride acid addition salt has higher bioavailability than its free base form at higher gastric pH conditions. According to related reports from FDA-review, the bioavailability of prasugrel hydrochloride or its free base form is about equal when the drugs are administrated alone. When prasugrel hydrochloride or its free base form is administrated together with PPI or H2 receptor antagonists (resulting in higher pH conditions), the bioavailability of the free base form is lower than the hydrochloride acid addition salt form. According to this disparity in solubility of prasugrel hydrochloride and its free base, it is desirable to improve the bioavailability of the free base form to overcome the solubility difficulties at different pH conditions.

DESCRIPTION OF THE INVENTION

As used herein, a solid dispersion refers to a dispersion system in which a drug is uniformly dispersed in a solid carrier such as molecular, colloidal, amorphous, and microcrystalline forms. Solid dispersion technology may increase the solubilization and dissolution rates of poorly soluble drugs, so as to improve the bioavailability of that drug. Solid dispersion products can also be prepared into capsules or tablets to further affect the commercial production of a drug product.

As used herein, a surfactant is an amphiphilic material having both hydrophilicity and lipophilicity. The surfactant can improve drug wettability, avoid drug particle coalescence, help with micellar solubilization, and thereby the solubility of hydrophobic drugs and improve their bioavailability. Surfactants can be divided into four categories: anionic surfactant, cationic surfactant, amphiphilic surfactant, and nonionic surfactant.

As used herein, an inclusion complex is a particular complex formed by all of or partly including a drug molecular structure into a molecular cavity of another substance. Inclusion is mainly a physical process, and its forming conditions depend on Van der Waals forces, scattered force, and dipole attractive forces. There are many preparation methods for inclusion complexes such as co-precipitation methods, grinding methods, ultrasonic methods, lyophilization methods, etc. Material performance with inclusion phenomenon mainly relate to cyclodextrins, cyclodextrins derivatives, and urea etc. The common cyclodextrins contain alpha, beta, and gamma types. Cyclodextrin inclusion techniques are applied more and more widely in the pharmacy, and are mainly used for effectively increasing the dissolution rate of poorly water-soluble drug, increasing the stability of unstable drug, masking excitant odor of drug products etc.

The invention disclosed herein to provides a pharmaceutical composition containing prasugrel and its salts, wherein prasugrel and its salts exist in a molecular, an ionic, a crystalline, or an amorphous form, wherein:

the pharmaceutical composition improves the dissolution rate of prasugrel and its salts at high pH;

the dissolution rate is equal to or higher than the dissolution rate of prasugrel hydrochloride;

the pH value is in the range of $1.0 < pH \leq 7.0$;

the composition contains surfactants;

prasugrel and its salts exist in the form of an inclusion complex, the inclusion complex comprising cyclodextrin or a derivative thereof, wherein the cyclodextrin is selected from β-CD and HP-β-CD, and preferably the cyclodextrin is β-CD, and wherein the weight ratio of prasugrel or its salts to cyclodextrin is 1:0.5 to 1:30, and preferably the weight ratio is 1:1-1:15, and more preferably the weight ratio is 1:1-1:5;

wherein prasugrel and its salt forms exist in a solid dispersion, wherein the composition also contains a hydrophilic carrier material, wherein the hydrophilic carrier material is selected from povidone (PVP), polyethylene glycols, mannitol, cellulose and/or cyclodextrin and derivative thereof, preferably selected from PVP, cellulose, and mannitol, more preferably selected from PVP, most preferably selected from PVP-K12 and PVP-K30; wherein the weight ratio of prasugrel and its salts to the carrier material is in the range of 1:1-1:20, preferably in the range of 1:1-1:10, more preferably in the range of 1:3-1:5;

and wherein the pharmaceutical composition is a solid, the solid preparation characterized in that:

(1) 90% of particle size of the drug is less than or equal to 75 μm; and (2) includes one or more surfactants;

wherein the particle size is preferably less than or equal to 50 μm, more preferably less than or equal to 10 μm, most preferably less than or equal to 5 μm, and the surfactant is selected from sodium dodecyl sulfate, bile salt, tween, span, polyoxyethylene or/and poloxamer, preferably the surfactant is selected from sodium dodecyl sulfate, bile salt or/and poloxamer, more preferably the surfactant is sodium dodecyl sulfate; wherein the weight ratio of prasugrel and its salts to the surfactant is less than or equal to 1:20, preferably less than or equal to 1:10, more preferably less than or equal to 1:2; and the composition may also contain fillers, wherein the filler is selected from: mannitol, starch, modified starch, microcrystalline cellulose, lactose or/and calcium hydrophosphate, preferably selected from a combination of mannitol and microcrystalline cellulose; and the composition may also contains lubricant, wherein the lubricant is selected from: metallic stearates, stearic acid, hydrogenated vegetable oil, talcum powder or/and colloidal silicon dioxide, preferably selected from a combination of colloidal silicon dioxide and magnesium stearate; wherein based on the total weight of the solid preparation being 100%, the weight ratio of the colloidal silicon dioxide is 0%-5%, preferably 0%-3%, more preferably 0%-2%, and the weight ratio of the magnesium stearate is 0.5%-1%.

This invention also provides a preparation method of the above-identified inclusion complex, wherein the method is selected from co-precipitation method, knead method, ultrasound method, lyophilization method, and spray drying method, preferably selected from co-precipitation method, knead method and lyophilization method, more preferably selected from co-precipitation method and knead method; and wherein the inclusion material used is cyclodextrin and its derivative which is preferably selected from β-CD and its derivatives and most preferably is β-CD.

This invention also provides a preparation method for the solid dispersion mentioned above, wherein the method is selected from solvent method, melting method, solvent-melting method and grinding method, preferably selected from solvent method and grinding method, more preferably is solvent method; wherein the solvent is selected from acetone, ethanol, methanol, ethyl acetate, methylene chloride, chloroform, DMF or/and ethyl ether, preferably selected from acetone, ethanol, methanol, ethyl acetate or/and methylene chloride, more preferably selected from acetone or/and ethanol.

After being prepared by only micronization, the dissolution rate of prasugrel at pH4.5 and pH6.8 conditions was improved, but there is still a gap, compared to that of prasugrel hydrochloride prepared by only micronization.

Compositions of this invention are prepared through the following steps:

1. Preparation of Solid Dispersion

The hydrophilic carrier may include PVP, polyethylene glycols, surfactant, mannitol, cellulose and cyclodextrin or its derivatives. According to different viscosity properties, PVP is divided into PVP-K12, PVP-K-17, PVP-K25, PVP-K29/32, PVP-K90, PVPP, and CPVD. According to different molecular weights, PEG used as solid dispersion is divided into PEG4000, PEG6000, PEG12000, and PEG20000.

According to electric charge, the surfactant used is divided into cationic surfactant, anionic surfactant, amphiphilic surfactant. The anionic surfactant can be sodium dodecyl sulfate, sodium stearate, hexadecanol sodium sulfate, diethyl succinic acid sulfonic acid sodium, sodium dodecyl benzene sulfonate and bile salt. The non-ionic surfactant can be Span, Tween, polyoxyethylene and poloxamer etc.

Because of the poor solubility of drugs, non-aqueous solvent is needed in the preparation of solid dispersions. In this invention, the use of common organic solvents such as acetone, ethanol, methylene chloride, methanol, chloroform, ethyl acetate, methanol, DMF and ether were studied.

(1) Solvent method for preparing solid dispersion: taking a carrier material and a drug with the ratio of 1:1-1:20 respectively, adding an appropriate organic solvent, mixing the solution uniformly under stirring, rotatably evaporating for 0.1-5 hours in a water bath with 25-65° C., then vacuum drying it for 5-30 hours at a temperature of 25-60° C., grinding and then screening the material through a 60-120 mesh sieve.

(2) Spray drying method for preparing solid dispersion: taking a carrier material and a drug with the ratio of 1:1-1:20 respectively, adding an appropriate organic solvent, mixing the solution uniformly under stirring and then drying with a spry dryer.

(3) Grinding method for preparing solid dispersion: taking a carrier material and a drug with the ratio of 1:1-1:20, mixing them uniformly, placing them in a mortar, a ball mill, or a colloid mill, grinding them together, taking them out, and screening them through a 80-100 mesh sieve.

The resulting solid dispersion can be made into tablets, capsules and granules etc. A glidant and a lubricant can be added in the preparation of the tablets or capsules, wherein the glidant and the lubricant comprise talcum powder, polyethylene glycol, colloidal silica, magnesium stearate and sodium dodecyl sulfate or mixture thereof. The weight of the glidant and the lubricant is 0.1%-5% of the tablets or capsules. A disintegrant can also be added, such as croscarmellose sodium, polyvinylpolypyrrolidone cross-linked, and sodium carboxymethyl starch. Filler can also be added, such as starch, modified starch, mannitol, and microcrystalline cellulose.

2. Adding a Surfactant to the Pharmaceutical Composition

After being prepared by only micronization, the dissolution rate of the prasugrel hydrochloride compared to the dissolution rate of prasugrel free base is improved, but at pH 6.8, the solubility of prasugrel free base is poorer than that of prasugrel hydrochloride. The dissolution rate of micronized prasugrel at higher pH can be equal to or higher than that of the preparation of micronized prasugrel hydrochloride by adding a certain amount of a surfactant.

Surfactants are well known to one skilled in the art, and divided into anionic surfactant such as sodium dodecyl sulfate and bile salt and non-ionic surfactant such as Tween, Span, polyoxyethylene and poloxamer. In order to improve the solubility of prasugrel, the surfactant is preferably selected from sodium dodecyl sulfate, bile salt and poloxamer, more preferably selected from sodium dodecyl sulfate and bile salt, and most preferably is sodium dodecyl sulfate.

In this invention, the particle size of the drug was also studied. The study found that with smaller particle sizes, the dissolution rate of prasugrel improves. In particular, when the drug particle size of less than or equal to 75 μm, preferably less than or equal to 50 μm, more preferably less than or equal to 10 μm, more preferably less than or equal to 5 μm are beneficial.

In this invention, the amount of the surfactant was also studied. The study found that when the weight ratio of prasugrel to the surfactant is less than or equal to 1:20, preferably less than or equal to 1:10, more preferably less than or equal to 1:2, better solubility of prasugrel was obtained.

In some embodiments, a filler is included. The filler is selected from mannitol, starch, modified starch, microcrystalline cellulose, lactose or/and calcium hydrophosphate, preferably selected from a combination of mannitol and microcrystalline cellulose.

In some embodiments, a lubricant is included. The lubricant is selected from metallic stearates, stearic acid, hydrogenated vegetable oil, talcum powder or/and colloidal silicon dioxide, preferably selected from a combination of colloidal silicon dioxide and magnesium stearate. The weight ratio of said aerosil (fumed silica) is 0%-5%, preferably 0%-3%, more preferably 0-2%. The weight ratio of magnesium stearate is 0.5%-1%.

The preparation method can be by dry-granulation technology. All the ingredients including the active ingredient and the surfactant except the lubricant are pre-mixed together, the mixture is screened by a sieve and compressed, the lubricant is added, and then the mixture is compressed into tablets or directly filled into capsules. When the surfactant is oily or semisolid, the surfactant can be mixed with microcrystalline cellulose or aerosol. After sieving, the mixture is mixed with prasugrel, and then dry-granulation is carried out.

The preparation method can be by wet-granulation. All the ingredients including the active ingredient, namely prasugrel, and the surfactant except for the lubricant are mixed together, the mixture is wetted with purified water and dried, or the surfactant is added into purified water as a wetting agent, then the mixture is granulated and dried. After mixing with the lubricant, the mixture is compressed into tablets or filled into capsules.

The preparation method can also be by direct tableting method. All the ingredients except for the lubricant are mixed together. After sieving and mixing, the lubricant is added, and the mixture is compressed directly into the tablets or filled into the capsules.

3. Preparation of Inclusion Complex (1) Saturated water solution method for preparing inclusion complex includes the following steps: preparing saturated solution of inclusion materials, maintaining the temperature of the solution at 40° C., dissolving prasugrel in acetone and dripping it into the saturated solution of inclusion materials under stirring. After stirring the solution for 8 hours under constant temperature, the mixture was cooled down to precipitation. The precipitate was filtered with Buchner funnel, washing with ethyl ether, and removal of water and organic solvent under reduced pressure.

(2) Grinding method for preparing inclusion complex includes the following steps: placing the inclusion material in a mortar, adding an appropriate amount of water, grinding the inclusion material uniformly, and then adding micronized prasugrel in the mortar and grinding them together to obtain a paste, followed by drying, washing, and drying under reduced pressure.

The inclusion material is selected from β-cyclodextrin (β-CD) and its derivatives, preferably selected from β-CD. The solvent is acetone, anhydrous ethanol, dichloromethane, methanol or chloroform etc.

This invention also includes inclusion by using heterogeneous systems, but the result showed the effect of this form of inclusion is poor.

All the solid dispersion and inclusion complexes of prasugrel prepared by the technology in this invention are intermediates for formulation and can be prepared into capsules or tablets directly, too.

The capsules or tablets prepared from the intermediates of solid dispersion or inclusion can contain a filler selected from mannitol, starch, modified starch, microcrystalline cellulose, sorbitol and cane sugar. Except for active ingredient and filler, the pharmaceutical solid unit dosage form can contain a variety of other conventional excipients such as a disintegrating agent and a small amount of lubricant. The lubricant comprises metallic stearates (Mg, Ca, Na), stearic acid, wax, hydrogenated castor oil, talcum powder and colloidal silicon dioxide. The disintegrating agent comprises sodium carboxymethyl starch, croscarmellose sodium, polyvinlypolypyrrolidone (PVPP), low substituted hydroxypropylcellulose, modified maize starch, pregelatinized starch and native starch.

The preparation technology of solid dispersion and inclusion complex of prasugrel free base can be used direct in tableting process or dry granulation process.

In this invention, the prasugrel and hydrophilic carrier material were used as starting materials to improve the drug product's dissolution rate of the prasugrel and its salts at high pH by adding surfactants, using solid dispersion technology or inclusion technology, thereby to improve the bioavailability of prasugrel base at high pH. Drug products with prasugrel prepared by the methods disclosed herein have the following advantages:

(1) The bioavailability of prasugrel at high pH is improved by adding surfactants, using solid dispersion technology or inclusion technology in the formulation. The dissolution rate of prasugrel is similar to or higher than that of prasugrel hydrochloride at high pH.

(2) The intermediates of prasugrel solid dispersion and inclusion complex can be further prepared into capsules and tablets for commercial production of desired drug products.

PREFERRED EMBODIMENTS

The invention will be illustrated specifically by the following embodiments. These embodiments are used to illustrate the invention, and no limitations to scope of the claimed invention are intended.

Example 1

| Pharmaceutical composition: | |
| --- | --- |
| Drug (prasugrel) | 5 g |
| Sodium dodecyl sulfate | 10 g |
| Mannitol | 73 g |
| Microcrystalline cellulose | 50 g |
| Cross-linked carboxymethyl cellulose sodium | 7.5 g |
| Hydroxypropyl methyl cellulose | 3 g |
| Magnesium stearate | 1.5 g |

Preparation Process:

The drug (prasugrel) was micronized, mixed with sodium dodecyl sulfate. Microcrystalline cellulose, mannitol, cross-linked sodium carboxymethyl cellulose, and hydroxypropyl methyl cellulose were added successively through equal increment. The mixture was screened through a 60 mesh sieve for 5 times. Magnesium stearate (pretreated by screening through a 60 mesh sieve) was added last, and the mixture was mixed uniformly, then compressed to tablet form.

Example 2

| Pharmaceutical composition: | |
| --- | --- |
| Drug (prasugrel) | 5 g |
| Sodium dodecyl sulfate | 5 g |
| Mannitol | 71.5 g |
| Microcrystalline cellulose | 50 g |
| Cross-linked carboxymethyl cellulose sodium | 7.5 g |
| Hydroxypropyl methyl cellulose | 3 g |
| Aerosil | 1.5 g |
| Magnesium stearate | 1.5 g |

Preparation Process:

The drug (prasugrel) was micronized, mixed with other excipients except for the surfactant and the lubricant. Sodium dodecyl sulfate was dissolved in purified water, and the solution was used as a wetting agent. The wetting agent was added to the mixed excipients to prepare a damp mass. The damp mass was screened through 30 mesh sieve to granulate form and dried. Magnesium stearate was added after the mixture was screened through a 40 mesh sieve, and then the mixture was compressed to tablet form.

Example 3

| Pharmaceutical composition: | |
| --- | --- |
| Drug (prasugrel) | 5 g |
| Poloxamer | 5 g |
| Mannitol | 70 g |
| Microcrystalline cellulose | 50 g |
| Cross-linked carboxymethyl cellulose sodium | 7.5 g |
| Hydroxypropyl methyl cellulose | 3 g |
| Aerosil | 3 g |
| Magnesium stearate | 1.5 g |

Preparation Process:

The drug (prasugrel) was micronized, mixed with other excipients except for the surfactant and the lubricant. Poloxamer was dissolved in purified water, and it was used as a wetting agent. The wetting agent was added to the mixed excipients to prepare a damp mass. The damp mass was screened through a 30 mesh sieve to granulate form and dried. Magnesium stearate was added after the mixture was screened through a 40 mesh sieve, and then the mixture was compressed to tablet form.

Example 4

Pharmaceutical Composition:

| Drug:Carrier | 1:1 | 1:3 | 1:5 | 1:8 | 1:10 |
| --- | --- | --- | --- | --- | --- |
| Drug(prasugrel) | 2 g | 2 g | 2 g | 2 g | 2 g |
| PVPK30 | 2 g | 6 g | 10 g | 16 g | 20 g |
| Acetone | 30 ml | 30 ml | 45 ml | 60 ml | 90 ml |
| Anhydrous ethanol | 5 ml | 10 ml | 15 ml | 20 ml | 30 ml |

Preparation Process:

The drug (prasugrel) was dissolved in acetone. PVPK30 was used as a carrier material that was dissolved in anhydrous ethanol. The solutions of the drug and carrier material were mixed together, evaporated in a 40° C. water bath with a rotavapor. The mixture was dried under vacuum for 24 hours at 40° C., ground and screened through a 80 mesh sieve to solid dispersion form.

Example 5

Pharmaceutical Composition

| Drug:Carrier | 1:1 | 1:3 | 1:5 | 1:8 | 1:10 |
| --- | --- | --- | --- | --- | --- |
| Drug(prasugrel) | 2 g | 2 g | 2 g | 2 g | 2 g |
| PVPK30 | 2 g | 6 g | 10 g | 16 g | 20 g |
| Acetone | 30 ml | 30 ml | 45 ml | 60 ml | 90 ml |
| Anhydrous ethanol | 5 ml | 10 ml | 15 ml | 20 ml | 30 ml |
| PVPP | 24 g | 40 g | 45 g | 60 g | 84 g |

Preparation Process:

The drug (prasugrel) was dissolved in acetone. PVPK30 was used as a carrier material that was dissolved in anhydrous ethanol. The ethanol solution of PVPK30 was added into acetone solution having the drug, and mixed together. The mixed solution was added into PVPP as a binder, then uniformly dispersed, and the mixture was evaporated in a 40° C. water bath with a rotavapor. The mixture was dried under vacuum for 24 hours at 40° C., ground and screened through a 80 mesh sieve to solid dispersion form.

Example 6

Pharmaceutical Composition:

| Drug (prasugrel) | 2 g |
| --- | --- |
| Acetone | 100 ml |
| PVPK30 | 20 g |
| Anhydrous ethanol | 50 ml |

Preparation Process

The drug (prasugrel) was dissolved in acetone. PVPK30 was used as a carrier material that was dissolved in ethanol. The two solutions were mixed together. A solid dispersion was obtained through spray-drying method.

Example 7

Pharmaceutical Composition:

| Drug (prasugrel) | 1 g |
| --- | --- |
| Acetone | 50 ml |
| PEG6000 | 3 g |

Preparation Process:

PEG6000 was dissolved in acetone at 40° C., followed by addition of the drug was after cooling. The mixture was stirred rapidly until homogenous, and then precipitated after cooling.

Example 8

Pharmaceutical Composition:

| Drug (prasugrel) | 1 g |
| --- | --- |
| Mannitol | 15 g |

Preparation Process:

Micronized drug (prasugrel) and mannitol were added into a ball mill and ground for 6 hours. The mixture was taken out and screened through a 80 mesh sieve to obtain a solid dispersion.

Example 9

Pharmaceutical Composition:

| Drug (prasugrel) | 1 g |
| Mannitol | 10 g |
| Microcrystalline cellulose | 5 g |

Preparation Process:

The drug (prasugrel), mannitol, and microcrystalline cellulose were added into a ball mill and ground for 6 hours. The mixture was taken out and screened through a 80 mesh sieve to obtain a solid dispersion.

Example 10

Pharmaceutical Composition:

| drug:carrier | Drug:β-CD (1:1) | Drug:β-CD (1:3) | Drug:β-CD (1:5) |
|---|---|---|---|
| Drug (prasugrel) | 5 g | 2 g | 1 g |
| Acetone | 80 ml | 40 ml | 20 ml |
| β-CD | 5 g | 6 g | 5 g |
| water | 140 ml | 176 ml | 140 ml |

Preparation Process:

At 40° C., β-CD was prepared into a saturated solution. The drug (prasugrel) was dissolved in acetone, and dropped into the β-CD saturated solution under stirring. The mixture was dispersed for 8 hours, and the temperature was maintained at 40° C. After cooling, the solid was precipitated, filtered, washed with ether, and dried to obtain the prasugrel inclusion complex.

Example 11

Pharmaceutical Composition:

| drug:Carrier | Drug:β-CD (1:1) | Drug:β-CD (1:2) | Drug:β-CD (1:3) | Drug:β-CD (1:5) |
|---|---|---|---|---|
| Drug (prasugrel) | 2 g | 1 g | 0.665 g | 0.526 g |
| acetone | 2 g | 2 g | 1.995 g | 2.63 g |
| β-CD | 6 ml | 6 ml | 5.99 ml | 7.89 ml |

Preparation Process:

The β-CD was placed into a mortar followed by three additions of water. The drug (prasugrel) was weighed and placed into the mortar. The materials were ground together until the mixture looked pasty. The mixture was washed and dried to obtain the prasugrel inclusion complex.

Test Example 1

PVP was used as the carrier material. The solid dispersion is prepared by solvent method (drug:carrier=1:10), and the method to evaluate solubility in vitro is given as follows:

(1) A solid dispersion which contains the drug substance (prasugrel) 5 mg, according to the method of solubility test and 1000 ml at pH 4.5 phosphate buffer was used as dissolution medium, with a rotating speed of 50 turns per minute. Using this method, 5 ml of the solution was taken at 5 min, 10 min, 15 min, 20 min, 30 min, 45 min, and 60 min (5 ml dissolution medium was supplemented after the 5 ml solution was taken out) and filtered. The filtrate was taken as the test solution and checked for purity using HPLC.

(2) A solid dispersion which contains the drug substance 5 mg, according to the method of dissolution rate test and 1000 ml at pH 6.8 phosphate buffer was used as dissolution medium, with a rotating speed of 50 turns per minute. Using this method, 5 ml of the solution was taken at 5 min, 10 min, 15 min, 20 min, 30 min, 45 min, and 60 min (5 ml dissolution medium was supplemented after the 5 ml solution was taken out) and filtered. The filtrate was taken as the test solution and checked for purity using HPLC.

(3) A control of prasugrel hydrochloride was prepared as follows:

| prasugrel hydrochloride | 5.49 g |
| Mannitol | 79.51 g |
| Microcrystalline cellulose | 50 g |
| Cross-linked carboxymethyl cellulose sodium | 7.5 g |
| Hydroxypropyl methyl cellulose | 3 g |
| Aerosil | 3 g |
| Magnesium stearate | 1.5 g |

Preparation Process:

The control drug (prasugrel hydrochloride) was micronized, added successively with microcrystalline cellulose, mannitol, cross-linked carboxymethyl cellulose sodium, and hydroxypropylmethyl cellulose and mixed. The mixture was screened through a 60 mesh sieve five times. Magnesium stearate (pretreated by screening through a 60 mesh sieve) was added last, and the mixture was mixed uniformly and compressed directly to tablet form.

The dissolution rate of examples 1-11 were evaluated by the evaluation system mentioned above. The results of the dissolution rate showed that the dissolution rate of prasugrel solid preparation was improved significantly. Comparative data for the dissolution rate of the products in examples 1, 5, and 10 and the control drug (prasugrel hydrochloride) tablet at pH 4.5 and 6.8 is shown here.

The dissolution rate was evaluated in pH 4.5 phosphate buffer:

TABLE 1

Prasugrel hydrochloride vs. product of example 1

| | 0 min | 5 min | 10 min | 15 min | 20 min | 30 min |
|---|---|---|---|---|---|---|
| Prasugrel hydrochloride | 0 | 16.71 | 26.66 | 32.45 | 36.78 | 43.42 |
| Product of example 1 | 0 | 25.73 | 53.76 | 56.93 | 59.15 | 60.28 |

TABLE 2

Prasugrel hydrochloride vs. product of example 5

| | 0 min | 5 min | 10 min | 15 min | 20 min | 30 min |
|---|---|---|---|---|---|---|
| Prasugrel hydrochloride | 0 | 16.71 | 26.66 | 32.45 | 36.78 | 43.42 |
| Product of example 5 (Prasugrel:Carrier = 1:1) | 0 | 15.43 | 27.47 | 35.71 | 49.77 | 52.00 |
| Product of example 5 (Prasugrel:Carrier = 1:3) | 0 | 41.30 | 46.66 | 49.91 | 59.45 | 61.96 |

TABLE 2-continued

Prasugrel hydrochloride vs. product of example 5

|  | 0 min | 5 min | 10 min | 15 min | 20 min | 30 min |
|---|---|---|---|---|---|---|
| Product of example 5 (Prasugrel:Carrier = 1:5) | 0 | 58.51 | 62.89 | 63.97 | 64.12 | 66.70 |
| Product of example 5 (Prasugrel:Carrier = 1:8) | 0 | 60.13 | 64.57 | 65.92 | 67.45 | 68.37 |
| Product of example 5 (Prasugrel:Carrier = 1:10) | 0 | 65.98 | 71.73 | 72.14 | 72.57 | 73.86 |

TABLE 3

Prasugrel hydrochloride vs. product of example 10

|  | 0 min | 5 min | 10 min | 15 min | 20 min | 30 min |
|---|---|---|---|---|---|---|
| Prasugrel hydrochloride | 0 | 16.71 | 26.66 | 32.45 | 36.78 | 43.42 |
| Product of example 10 (Prasugrel:β-CD = 1:1) | 0 | 22.6 | 29.48 | 36.46 | 39.46 | 41.18 |
| Product of example 10 (Prasugrel:β-CD = 1:3) | 0 | 52.16 | 61.6 | 64.1 | 64.89 | 68.67 |
| Product of example 10 (Prasugrel:β-CD = 1:5) | 0 | 36.83 | 45.09 | 52.23 | 55.88 | 61.32 |

The dissolution rate was evaluated in pH6.8 phosphate buffer:

TABLE 4

Prasugrel hydrochloride vs. product of example 1

|  | 0 min | 5 min | 15 min | 30 min | 45 min | 60 min |
|---|---|---|---|---|---|---|
| Prasugrel hydrochloride | 0 | 13.69 | 21.03 | 23.99 | 25.13 | 25.62 |
| Product of example 1 | 0 | 17.31 | 24.92 | 29.57 | 34.32 | 36.97 |

TABLE 5

Prasugrel hydrochloride vs. product of example 5

|  | 0 min | 5 min | 15 min | 30 min | 45 min | 60 min |
|---|---|---|---|---|---|---|
| Prasugrel hydrochloride | 0 | 13.69 | 21.03 | 23.99 | 25.13 | 25.62 |
| Product of example 5 (Prasugrel:Carrier == 1:1) | 0 | 11.67 | 15.12 | 19.36 | 24.72 | 25.86 |
| Product of example 5 (Prasugrel:Carrier = 1:3) | 0 | 17.82 | 25.51 | 29.09 | 34.57 | 35.80 |
| Product of example 5 (Prasugrel:Carrier = 1:5) | 0 | 20.58 | 26.42 | 32.90 | 36.12 | 40.97 |
| Product of example 5 (Prasugrel:Carrier = 1:8) | 0 | 21.08 | 28.59 | 34.58 | 37.05 | 42.72 |
| Product of example 5 (Prasugrel:Carrier = 1:10) | 0 | 25.6 | 33.76 | 37.27 | 39.48 | 47.47 |

TABLE 6

Prasugrel hydrochloride vs. product of example 10

|  | 0 min | 5 min | 15 min | 30 min | 45 min | 60 min |
|---|---|---|---|---|---|---|
| Prasugrel hydrochloride | 0 | 13.69 | 21.03 | 23.99 | 25.13 | 25.62 |
| Product of example 10 (Prasugrel:β-CD = 1:1) | 0 | 14.87 | 22.43 | 25.66 | 26.87 | 26.84 |

TABLE 6-continued

Prasugrel hydrochloride vs. product of example 10

|  | 0 min | 5 min | 15 min | 30 min | 45 min | 60 min |
|---|---|---|---|---|---|---|
| Product of example 10 (Prasugrel:β-CD = 1:3) | 0 | 15.74 | 25.41 | 28.76 | 29.31 | 30.15 |
| Product of example 10 (Prasugrel:β-CD = 1:5) | 0 | 16.74 | 26.24 | 27.28 | 28.37 | 29.27 |

What is claimed is:

1. A pharmaceutical composition, comprising:
prasugrel and a surfactant, the surfactant comprising sodium dodecyl sulfate, wherein the surfactant is present in a weight proportion to prasugrel between about 1:1 and about 10:1, the pharmaceutical composition in the form of a solid preparation, wherein the pharmaceutical composition has a faster dissolution rate than prasugrel at a pH of between about 1 and 7.

2. The composition of claim 1, wherein the dissolution rate of the composition is faster than the solubility of prasugrel hydrochloride.

3. The composition of claim 1 in the form of a solid dispersion.

4. A method for preparing the pharmaceutical composition of claim 3, wherein the method is selected from solvent method, melting method, solvent-molten method, and grinding method.

5. The method of claim 4, wherein the solvent is selected from acetone, ethanol, methanol, ethyl acetate, methylene chloride, chloroform, DMF and ethyl ether.

6. The composition of claim 3, further comprising a hydrophilic carrier.

7. The composition of claim 6, wherein the weight ratio of prasugrel to the carrier is in the range of about 1:1 to about 1:20.

8. The composition of claim 6, wherein the hydrophilic carrier is selected from povidone, polyethylene glycols, mannitol, cellulose, and cyclodextrin and cyclodextrin derivatives.

9. The composition of claim 8, wherein the hydrophilic carrier is selected from povidone-K12 and povidone-K30.

10. The composition of claim 1, wherein:
90% of the particle size of prasugrel is less than or equal to 75 μm.

11. The composition of claim 1, wherein the solid preparation contains a filler.

12. The composition of claim 11, wherein the filler is selected from: mannitol, starch, modified starch, microcrystalline cellulose, lactose, and calcium hydrophosphate.

13. The composition of claim 1, further comprising a lubricant.

14. The composition of claim 13, wherein the lubricant is selected from: metallic stearates, stearic acid, hydrogenated vegetable oil, talcum powder, and colloidal silicon dioxide.

15. The composition of claim 14, wherein the weight percent concentration of the colloidal silicon dioxide is less than 5%.

16. The composition of claim 14, wherein in relation to the total weight of the solid preparation being 100%, the weight concentration of the metallic stearate is 0.5%-1%.

17. The composition of claim 1, wherein the surfactant is present in a weight proportion to prasugrel of about 1:1.

18. The composition of claim 1, wherein the surfactant is present in a weight proportion to prasugrel between about 1:1 and about 2:1.

19. An inclusion complex composition, comprising:
prasugrel and an inclusion material selected from cyclodextrin and cyclodextrin derivatives, wherein the inclusion material is present in a weight proportion to prasugrel between about 1:1 and about 15:1.

20. A method for preparing the composition of claim 19, wherein the method is selected from co-precipitation method, knead method, ultrasound method, lyophilization method, and spray drying method.

21. The composition of claim 19, wherein the cyclodextrin and cyclodextrin derivative is selected from cyclodextrin, β-cyclodextrin and hydroxypropyl-β-cyclodextrin.

22. The composition of claim 21, wherein the inclusion material is cyclodextrin.

* * * * *